United States Patent [19]

Taboada et al.

[11] Patent Number: 5,364,390
[45] Date of Patent: Nov. 15, 1994

[54] HANDPIECE AND RELATED APPARATUS FOR LASER SURGERY AND DENTISTRY

[75] Inventors: John Taboada; Robert H. Poirier, both of San Antonio, Tex.

[73] Assignee: Refractive Laser Research and Development, Inc., Fremont, Calif.

[21] Appl. No.: 869,834

[22] Filed: Apr. 16, 1992

Related U.S. Application Data

[63] Continuation of Ser. No. 715,014, Jun. 13, 1992, abandoned, which is a continuation of Ser. No. 571,822, Aug. 22, 1990, abandoned, which is a continuation of Ser. No. 195,843, May 19, 1988, abandoned.

[51] Int. Cl.$^5$ .............................................. A61K 5/06
[52] U.S. Cl. ......................................... 606/10; 606/3; 606/4; 606/5; 433/215
[58] Field of Search ............... 128/345, 347, 398, 895; 606/3-14; 604/20, 22, 27; 433/215

[56] References Cited

U.S. PATENT DOCUMENTS

| | | | |
|---|---|---|---|
| 3,315,680 | 4/1967 | Silbertrust et al. | 128/395 |
| 3,547,125 | 12/1970 | Tagnon | 128/303.1 |
| 3,821,510 | 6/1974 | Muncheryan | 128/395 |
| 3,865,113 | 2/1975 | Sharon et al. | 606/18 |
| 4,273,109 | 6/1981 | Enderby | 606/15 |
| 4,470,407 | 9/1984 | Hussein | 128/398 |
| 4,559,942 | 12/1985 | Eisenberg | 128/303.1 |
| 4,620,769 | 11/1986 | Tsuno | 128/6 |
| 4,621,283 | 11/1986 | Feinbloom | 128/22 |
| 4,622,971 | 11/1986 | Yamamoto | 128/395 |
| 4,712,543 | 12/1987 | Baron | 606/5 |
| 4,719,912 | 1/1988 | Weinberg | 128/395 |
| 4,729,373 | 3/1988 | Peyman | 606/4 |
| 4,770,653 | 9/1988 | Shturman | 604/21 |
| 4,784,135 | 11/1988 | Blum et al. | 606/3 |
| 5,048,946 | 9/1991 | Sklar et al. | 606/4 |

FOREIGN PATENT DOCUMENTS

| | | | |
|---|---|---|---|
| 31073 | 7/1981 | European Pat. Off. | 128/398 |
| 93005 | 11/1983 | European Pat. Off. | 219/121.79 |
| 3148748 | 7/1983 | Germany | 606/4 |
| 3623111 | 4/1987 | Germany | 606/4 |
| 260715 | 10/1989 | Japan | 200/293.1 |
| 8702884 | 5/1987 | WIPO | 600/3 |
| 9114411 | 10/1991 | WIPO | 606/4 |

*Primary Examiner*—David M. Shay
*Attorney, Agent, or Firm*—Irvin A. Lavine

[57] ABSTRACT

Apparatus is provided for effecting medical or dental surgery, and to a related method. A subject body on which surgery is to be performed has a reference thereon or therein identified, such as a layer in the cornea, or a surface of a tooth. A handpiece contains a variable focus lens, and a fiberoptic bundle is connected axially to the proximal end of the handpiece to illuminate the site. The image of the site is passed to a control apparatus for adjusting the variable focus lens so as to provide for focussing of the treatment laser beam at a predetermined distance from the reference.

A method of performing surgery comprising determining by focus condition measuring equipment the distance of a reference in a subject body, adjusting a variable focus lens by control signals proportional to the focus condition measured, and passing a laser beam through the variable focus lens in the adjusted position to provide a focus spot of the laser beam at a predetermined distance from the reference.

30 Claims, 2 Drawing Sheets

HANDPIECE AND RELATED APPARATUS FOR LASER SURGERY AND DENTISTRY

This application is a continuation of application Ser. No. 07/715,014, filed Jun. 13, 1992, now abandoned, which is a continuation of application Ser. No. 571,822, filed Aug. 22, 1990, now abandoned, which is a continuation of Ser. No. 195,843, filed May 19, 1988, now abandoned.

CROSS-REFERENCE TO RELATED APPLICATIONS

The present application is related to the followings applications of the present inventors:

Ser. No. 148,425 filed Jan. 25, 1988 Inventors: John Taboada and Robert H. Poirier METHOD AND APPARATUS FOR LASER SURGERY Ser. No. 149,917 filed Jan. 25, 1988 Inventors; John Taboada and Robert H. Poirier PHACO-EMULSIFICATION APPARATUS AND METHOD Ser. No. 160,007 filed Feb. 24, 1988 Inventors: John Taboada and Robert H. Poirier METHOD AND APPARATUS FOR CONTROLLING THE DEPTH OF CUT OF A LASER KNIFE

BACKGROUND OF THE INVENTION

The present invention relates to a handpiece and related apparatus for performing surgery and dentistry with a laser.

Applications of laser technology to medicine and dentistry have been suggested for well over a decade. Advances have been rapid, and laser devices are now commonly found, not only in operating rooms, but in the offices of physicians. Among the more widely used applications of laser technology in medicine is in the field of eye surgery.

Among the uses of lasers in the medical field are cutting, cauterizing, melting and ablating tissue. It has been recognized that to effect tissue, or other material to the greatest degree, one or more conditions must be met, including ( a ) the delivery of the laser energy in high powered pulses or with high continuous power; (b) the laser must be tuned to the extreme violet end of the spectrum where the photon absorption is high in organic substance; or (c) the laser must be tuned to the extreme infrared end of the spectrum where absorption of radiation by water, a major constituent of living tissue, is a factor. As is known, condition (a) functions through non-linear optical processes such as dielectric breakdown, which creates a finely localized absorption site because the resulting plasma is usually opaque to the laser beam. These noted conditions are extreme conditions and have resulted in the inability of some or all optical components to handle this extreme laser energy delivered.

In the care and treatment of eyes, it has been recognized that in some cases an eye may depart from a normal or "perfect" configuration, particularly in that the outer surface of the eye, the cornea, is not curved properly, but has some excessive steepness which cause kerataconus or myopia, resulting in impaired vision. Proposals have been made to correct this imperfection by changing the internal structure of the stroma layer of the cornea by the application of heat and/or radio frequency energy, but these proposals have had significant deficiencies. For example, Doss et al U.S. Pat. No. 4,326,529 attempts to achieve the correction of corneal irregularities by keratoplasty technique, in which the central stroma is heated with a radio frequency electrode probe, to break collagen crosslinks, to contract the collagen which is a part of the clear corneal medium. The method disclosed in Doss et al has the disadvantage that the heat deposition is not easily localized in the three-dimensional space of the cornea.

Roussell et al U.S. Pat. No. 4,409,979 provides apparatus for treating the human eye with laser radiation, and for viewing the site. Reflectors and prisms are provided to conduct light from a light source to the site, passing eccentric to the optical path; an image is conducted from the site to a viewing instrument, such as a microscope, centrally of the optical path. A beam from a laser is caused to strike the central part of a mirror which is movable between an operative position and a retracted position. In the operative position, the mirror directs the laser radiation to the site, generally along the optical path. In the retracted position, the mirror is removed from the optical path, permitting passage of the aforementioned light beam and observing beam. A weak laser is also provided, whose beam passes in a path eccentric to the optical path. A manually adjustable focussing lens is provided in the light paths to focus the light from the light source and the laser radiation. The arrangement presents a problem which requires the provision of a rotatable tube for housing beam splitters and reflectors which are part of the optical path of the light source beam, the observing beam, and the weak laser beam. Hence, manipulation of the rotatable tube and manual adjustment of the focussing lens are required to achieve the desired viewing and focussing, prior to the energization of the power laser and the moving of the mirror into operative position to direct the power laser beam to the site. The method of Roussell et al has the disadvantage that it cannot be moved with the freedom of a handpiece with six degrees of freedom. In addition, the method requires the intervention of an operator to establish the focal site of the laser energy delivery.

Muckerhide U.S. Pat. No. 4,316,467 discloses the use of a laser for treating birthmarks or lesions on the skin, in which control of the power or energy level of a laser is effected by receiving radiation reflected from the lesion by a fiberoptic bundle: a control circuit senses the intensity corresponding to the color intensity of the region to which the laser beam is directed and varies the energy of the laser.

Goldenberg U.S. Pat. No. 4,641,912 discloses an excimer laser system used for angioplasty, and includes a pair of optical fibers, one for obtaining an image of the atherosclerotic plaque to be ablated by the laser energy, a second optical fiber being provided for lasing the plaque. A video camera and monitor are utilized to acquire and display an image of the plaque.

Karlin et al U.S. Pat. No. 4,583,539 discloses a system for performing surgery on the eye using a $CO_2$ laser source and an articulated arm structure, the laser energy being delivered through a probe which is connected to the articulated arm structure and which is insertable into an eye.

Kimura U.S. Pat. No. 4,266,549 discloses a laser scalpel including a probe through which light may be directed to illuminate the optical site: where a tumor is to be subjected to lasing, a picture or graphic representation may be obtained. An adaptor is provided at the tip of the probe to engage the tissue at or adjacent the tumor, to establish the distance of the focussing lens of the probe to the tumor to be laser.

Remy et al U.S. Pat. No. 4,289,378 discloses an apparatus for adjusting the focal point of a working laser beam onto a microscopic target region of a transparent biological object. Use is made of an auxiliary laser beam having a wavelength within the visible range, and through joint manual focussing of the laser beams, the location of focussing of the working beam at a particular locus at a desired depth within the transparent biological specimen is achieved.

The aforementioned disclosures, however, lack provision for a direct contact plano convex lens for the delivery of the laser energy to loci at very small ranges from the surfaces. They also lack provision for a contact lens surface to cover the cornea while the adjacent lower tissue is being irradiated and also to serve as a guide surface for hand held instruments. These limitations are overcome by the present invention as will be made evident below.

Among the patents disclosing a dental handpiece for directing laser energy to a tooth is Ota et al U.S. Pat. No. 4,503,853. In this patent, the handpiece includes a centrally located optical fiber through which the laser beam is passed to the tooth. The handpiece is provided at its distal end with a distance spacer to engage the tooth and provide a fixed spacing between the tooth and the end of the optical fiber to regulate the amount and strength of irradiation of laser beams from the laser source. Myers et al U.S. Pat. No. 4,521,194 discloses a method of removing incipient carious lesions and/or stains from teeth by the application of a laser beam from a source such as a yttrium-aluminum-garnet laser. In neither of these patents is there provision for autofocussing of the laser beam, nor is there a provision for viewing the site through the handpiece. These aforementioned apparatus also lack provision for the delivery of high peak power TEM(oo) laser mode radiation, as this radiation would normally destroy the fiber-optic delivery devices. For example, five millijoules Q-switched YAG laser pulses would destroy the single mode fiber-optic ends.

SUMMARY OF THE INVENTION

An apparatus and method for performing laser surgery Is disclosed, in which a focussed laser beam is directed by a handpiece to an operational site, and is automatically focussed, so that the tissue modifying (ablation, cutting melting, etc.) effect of the laser beam is located at a desired locus along the axis of the beam in the subject body. The handpiece which is provided is supported by a novel articulated arm system which permits the handpiece to have six degrees of freedom. The novel arrangement which uses prisms permits the delivery of high peak power laser radiation ranging from the ultraviolet to the infrared. Within the handpiece there is provided a dichroic reflector which receives laser radiation passed through the articulating arm system from a laser source, the laser radiation (including a concentric alignment beam) entering the handpiece along an optical path at right angles to the optical path which is substantially coincident with the axis of the handpiece. A system of focussing lenses is provided in the handpiece. A light source is optically connected to the handpiece through a fiberoptic bundle, which is connected to the proximal end of the handpiece, light passing axially along the handpiece axis and through the dichroic reflector and the variable focus lens to the site, the observation light from the site passing through the focussing lens and the dichroic reflector into the fiberoptic bundle and to a control system which causes automatic focussing of the adjustable lens, to focus the laser radiation at a preselected depth in the subject body related to a reference or benchmark in the body, which may be, for example, the endothelial cell layer of a cornea. The control system may take the form of an image scanner which delivers a signal to an error signal generator having a reference signal source therein, and generating an error signal to an electromagnetic impulser which controls a fluid cylinder. The fluid cylinder has a piston in it moved by the electromagnetic impulser, and is connected by a flexible conduit to a variable volume chamber of the variable focus lens. The handpiece lower member may be rotated about the handpiece axis, and the handpiece is rotatable about the above mentioned lateral axis. The fiberoptic bundle and the fluid conduit are both flexible, permitting unrestrained movement of the handpiece.

Among the objects of the present invention is the provision of apparatus and method of laser surgery in which there is automatic focussing of a laser beam relative to the operational site.

Another object is the provision of such method and apparatus including a handpiece in which the depthwise positioning of the focus spot of a focussed laser beam is automatically controlled relative to a reference feature.

Another object of the present invention is to provide an apparatus which includes a handpiece for delivery of laser energy and for permitting observation of the site along the axis of the handpiece.

Another object of the present invention is to provide an apparatus and method which include a plano-convex sapphire lens with the plano side to the tissue to be treated.

A further object is to provide a thin hard contact lens to cover the cornea to serve as a guide surface.

Still another object of the present invention is the provision of an apparatus which provides to a surgeon simultaneous, superimposed images of an operating site, derived from direct observation through a viewing instrument, and from a superimposed video image acquired through a handpiece at the operational site.

A further object of the present invention is to provide an apparatus which delivers laser radiation to an operational site through a handpiece while providing the handpiece with six degrees of freedom of motion for orientation of the handpiece relative to the operational site.

Yet a further object of the present invention is the provision of an apparatus which delivers laser radiation to an operational handpiece with a minimum of encumbrance, minimum friction and inertia, and optimum counterbalancing using a single boom and a novel air bearing beam conduit.

Other objects and many of the attendant advantages of the present invention will be readily understood from consideration of the following specification, claims and drawings.

DESCRIPTION OF THE PREFERRED EMBODIMENT

Figures 1, 1A:
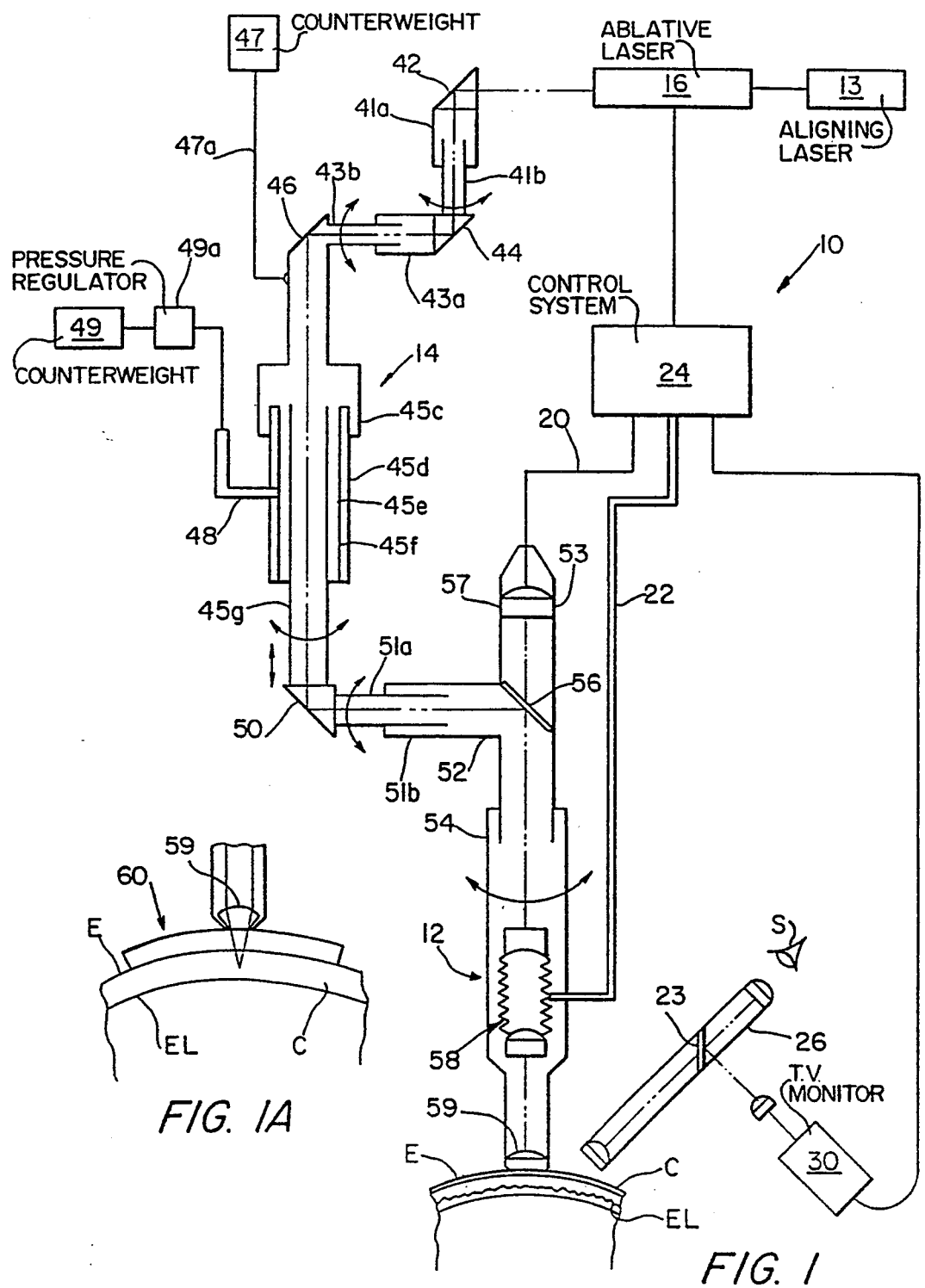
FIG. 1 is a schematic view of an apparatus in accordance with the present invention.
FIG. 1A is a detailed view of a part of the apparatus of FIG. 1, and a contact lens on a cornea.

Referring now to the drawings, wherein like or corresponding reference numerals are used for like or corresponding parts throughout the several views, there is shown in FIG. 1 an apparatus 10 for performing laser surgery on an eye E. There is shown, in particular, the transparent cornea C having within it the endothelial layer EL, and with a contact lens 60 on the cornea; the lens 60 is optional. The herein disclosed apparatus utilizes the depth of the endothelium as a reference or landmark for achieving the delivery of laser radiation at a concentrated focus spot within the cornea at a desired depth relative to the endothelium, regardless of the contour of the outer surface. Because the contact lens 60 has the novel arrangement of having the plano side to the cornea, the focussing is extremely accurate and localized. In order to locate the concentrated or focussed spot of the laser beam at the precise location, i.e., depth or distance from the corneal surface, the endothelial layer is utilized as a reference for a focussing system and a variable focus lens, described below. Although the herein disclosed method and apparatus are particularly applicable to treating the cornea with laser energy, the method and apparatus herein disclosed are not necessarily limited to that application.

The apparatus 10 includes a handpiece 12 adapted to be held in the hand of a surgeon. Handpiece 12 is supported by an articulating arm system 14, which receives energy from an ablative laser 16. There may also be provided a relatively weak, aligning laser 13. The laser 16 may be, for example, a high repetition rate, Q-switched YAG TEMoo mode system having an energy per pulse of about three millijoules and a rep rate of the order of 2,000 pulses per second. The laser 16 is coaxially traversed by the beam from the aligning laser 13, which is preferably a visible, low powered CW laser, and is used for achieving beam component alignment, or optionally as a source of illumination for the reference endothelial cell layer. Typically, the laser 13 is a three milliwatt helium neon laser. The laser beam in the Gaussian TEMoo mode can be diffraction limited focussed to a minimum spot size on the order of about 10 microns. The novel prism arrangement of the articulating system of the present invention permits any number of high power very ablative lasers to be used, such as an excimer laser for wavelengths in the far UV range, or an f-center laser for wavelengths in the near IR region. Preferably, a movable platform or carriage (not shown) supports the lasers 16 and 13 and the articulating arm system 14.

Connected to the handpiece 12 is a flexible coherent fiberoptic bundle 20 and a flexible conduit 22, which are in turn connected to a monitoring and control system 24. A viewing instrument 26, such as a microscope, is provided, containing a beam splitter 28, and having adjacent to it a TV monitor 30. A surgeon S views through this instrument as shown.

The articulating arm system 14 is shown in schematic form, and provides for six degrees of movement of the handpiece 12. There is provided an outer tube 41a which is fixed, and in practice extends upwardly from prism 42. An inner tube 41b is axially rotatable relative to the outer tube 41a. This permits the remainder of articulating arm system 14 to rotate in a horizontal plane. The outer tube 41a is suitably anchored and supported, as mentioned above, Fixedly connected at right angles to the inner tube 41b is an outer tube 43a, having within it a prism or other reflector 44. Axially rotatable in the outer tube 43a is an inner tube 43b. A tube 45a is connected at right angles to the inner tube 43b, and in it is a reflector 46. A counter-weight 47 is connected to the tube 45a by an arm 47a. Tube 45a has an enlarged end 45c in which is mounted a tube 45d, and within the tube 45d there is a perforated tube 45e of smaller diameter, providing a chamber 45f between them. Air or gas is supplied to the chamber 45f through a conduit 48 supplied with air from an air or gas source 49 through a pressure regulator 49a. An inner tube 45g is located within the perforated tube 45e, and is rotatably and axially movable, being supported on an almost frictionless air cushion between the inner tube 47b and the perforated tube 45e.

The inner tube 45g has at its outer end a reflector and is secured at right angles to an inner tube 51a, there being an outer tube 51b which is axially rotatable with respect to it. The outer tube 51b forms part of a T-shaped housing 52 which includes a tube 53 transverse to the tube 51b. A lower tubular member 54 is axially rotatable relative to the tube 53. Within the housing 53 are a beam turner, specifically a dichroic reflector 56, and adjacent the proximal end of handpiece 12 and within housing 53 is an imaging lens 57. Within the tubular member 54 is a variable focus lens generally designated 58 and at its distal end is a plano-convex coupling lens 59, the exterior plano side of coupling lens 59 being in engagement with the outer surface of cornea C. In FIG. 1A, the plano side of lens 59 is in engagement with the surface of a hard contact lens 60 through which the radiation passes and which serves as a guide surface.

Figure 2:
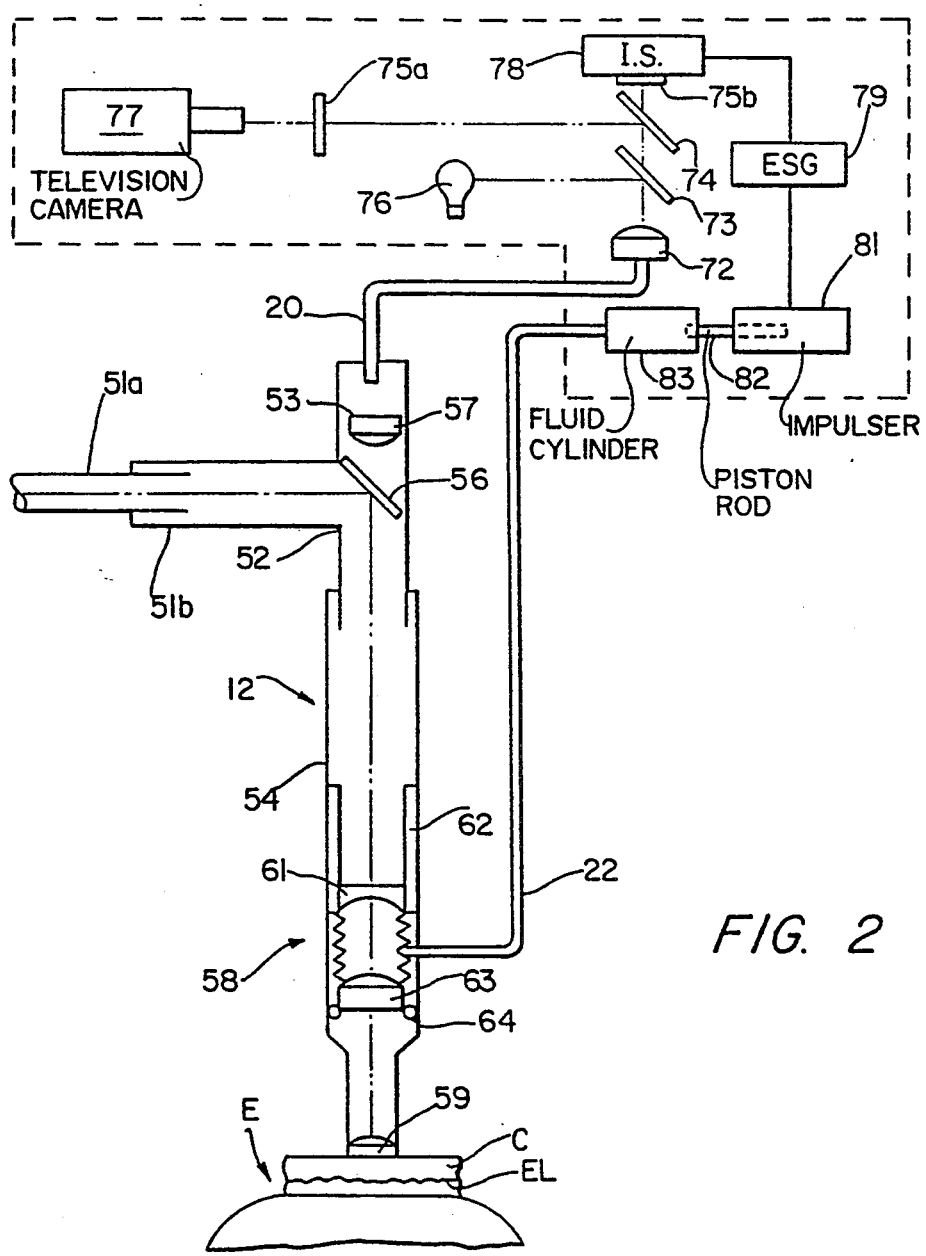
FIG. 2 is a schematic view showing portions of the apparatus of FIG. 1, in greater detail.

Referring now to FIG. 2, there is shown the handpiece 12, including the dichroic reflector 56, which is located at the juncture of an optical path through the tubes 51a and 51b, and an optical path along the axis of tubes 53 and 54. The variable focus lens 58 includes for example a negative lens 61 movable axially on guides 62, and a positive lens 63 fixed in position by a locking ring 64. A flexible bellows 66 is hermetically attached to the lenses 61 and 63: flexible conduit 22 extends from the flexible bellows 66, and is in fluid communication with the chamber formed by the lenses 61 and 63 and the flexible bellows 66.

The monitoring and control system 24 includes a lens 72 in alignment with an end of the fiberoptic bundle 20, and dichroic reflectors 73 and 74. A light source 76 is in alignment with dichroic reflector 73, and provides light to the operating site, through the lens 72, and fiberoptic bundle 20, and thence into the handpiece 12, passing through relay lens 57, dichroic reflector 56, the variable focus lens 58, and coupling lens 59. Alternatively, the illumination provided by the alignment laser 13 (FIG. 1) can serve to provide the image of the endothelial cells, in which case optical element 75a, 75b, which are bandpass filters passing only the wavelength of the alignment laser, are utilized. A television camera 77 is in alignment with the partial reflector 74, to receive images of the site, TV camera 77 being connected to the TV monitor 30 (FIG. 1).

Also forming a part of the monitoring and control system 24 is an image scanner 78, which receives an image from the endothelial layer EL. The image scanner 78, by means of out-of-focus sensings, measures the departure of the optical system comprised of the variable focus lens 58, and lenses 59 and 57 from focus on the reference layer EL, i.e., it measures the focus condition. The scanner 78 delivers a signal representative thereof to an error signal generator 79. Error signal generator 79 includes an internal reference standard, such as a pre-set voltage, and generates an error signal in proportion to the difference between the reference voltage and the voltage supplied from image scanner 78. The generated error signal is supplied to an electromagnetic impulser 81 which, in response to the signal received, moves a piston rod 82 into or out of a fluid cylinder 83. The fluid cylinder 83 is fluid connected with the variable volume chamber of variable focus lens 58 by the flexible conduit 22. Thus, the focus of the variable lens 58 is changed in accordance with the variation of the thickness of the cornea C. The automatic adjustment of the variable lens 58 with thickness variations of the cornea C assures that the laser beam focal point lies at a predetermined fraction of the corneal thickness since the focus condition of the variable lens system affects the surgical laser beam.

In use of the apparatus 10 shown in FIGS. 1 and 2 of the drawings and hereinabove described, the handpiece 12 is maneuvered into position so that the coupling lens 59 at the distal end thereof is in engagement with the outer surface of the cornea C of the eye E under observation and treatment, as shown in FIG. 1. Alternatively, as shown in FIG. 1A, the engagement surface may be a contact lens 60 positioned to cover the cornea and to provide a transparent guide surface. The positioning of handpiece 12 is facilitated by the articulating arm system 14, which permits six degrees of freedom of movement of handpiece 12. Thus, the handpiece 12 may be moved or translated, along three mutually perpendicular axes, and may be rotated about three mutually perpendicular axes. As will be appreciated, rotational movement will be effected by the axial rotational movement provided by the inner and outer tubes 41a, 41b, etc., and linear and rotational movement is facilitated by the structure including the tubes 45d and 45g, and the air bearing construction including the perforated tube 45e.

Assuming that the cornea C has a relatively normal thickness at the place where it is engaged by the coupling lens 59, the focus distance of the benchmark endothelial layer EL will be "normal" and consequently the image scanner will detect a sharp image of layer EL; when the signal generated by image scanner 78 is compared by error signal generator 79 with the internal reference standard, error signal generator 79 will not produce an error signal. Consequently, there will be no change made to the variable focus lens 58, and when the laser 16 is fired, there will be produced a very high energy density, highly localized spot, at a precise and automatically determined distance in relation to the endothelial layer EL. As may be desirable, the laser is not fired when the foregoing condition is not obtained. The handpiece 12 will be caused by the surgeon to move over the outer surface of the cornea C, for example in a radial path as in radial keratotomy, and assuming that it engages a thickness change, it will be apparent that the exterior plano end surface of coupling lens 59 will be moved away from the reference or benchmark endothelial layer EL. The image received by the image scanner 78 will be out of focus, and the image scanner 78 will therefore send a signal to the error signal generator 79 which will be different from the internal reference voltage of error signal generator 79. When a comparison is made, a difference between the two voltage signals occurs, and an error signal will be generated and sent to the electromagnetic impulser 81, resulting in movement of the piston rod 82, and a change in the focal length of the variable focus lens 58. The correction is accomplished in an extremely short period of time, so that the firing of the laser 16, which may, as is typical, be under the control of the surgeon, be accomplished without delay. The laser beam will be focussed so as to place the high energy, small diameter focus spot in the corneal layer at a desired, predetermined distance relative to the location of the endothelial layer EL.

The surgeon, utilizing both the handpiece 12 and the viewing instrument 26, will be able to obtain an image of the site which may be substantially the same as if he were looking into the distal end of the handpiece 12. The image of the site will pass from the site through the coupling lens 59, variable focus lens 58, dichroic reflector 56, and imaging lens 57; these lenses focus the image of the site onto the fiberoptic bundle 20, and the image passes through lens 72 to the beam splitter 74. The image will then pass to the TV camera 77, and be transmitted to the TV monitor 30, the image appearing via the beam splitter 28 occupies a small position of the viewing field in the viewing instrument 26. It will be appreciated that the viewing instrument 26 and the handpiece 12 may be maneuvered so as to be closely adjacent to each other, for viewing the same portion of the cornea C.

Figure 3:
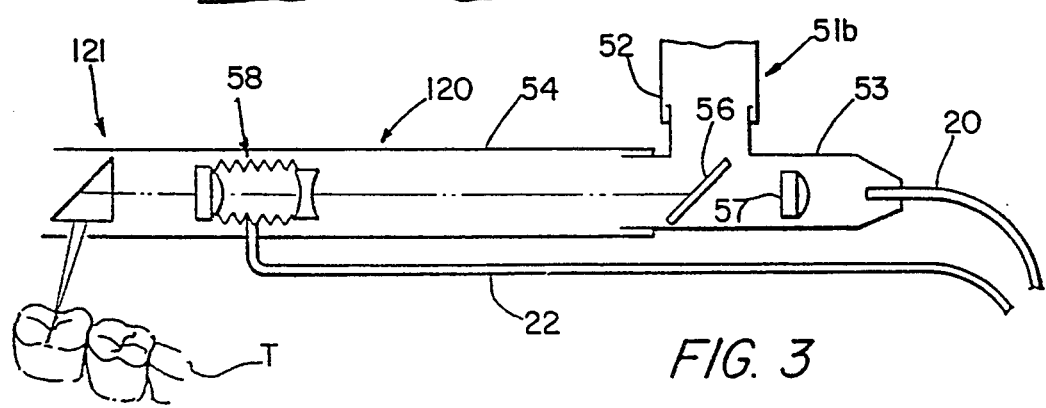
FIG. 3 is a view, partly in section, of a dental handpiece in accordance with the present invention.

Referring to FIG. 3, there is shown a handpiece 120 for dental applications, handpiece 120 being shown in conjunction with teeth T upon which dental work is to be performed. The handpiece 120 comprises T-shaped housing 52 formed by outer tube 51b and tube 53 transverse to it. Lower tubular member 54 is shown, rotatable with respect to tube 53, and having within it the variable focus lens 58. Also shown in handpiece 120 are the dichroic reflector 56 and imaging lens 57, with the fiberoptic bundle 20 connected to handpiece 120 at its proximal end. The conduit 22 is also shown, extending to the variable focus lens 58. At the distal end of handpiece 20, there is a reflector 121, which may take the form of a diverting prism. The diverting prism 121 will divert the light from the light source 76 to the target area on one of the teeth T, and the image thereof will be delivered to the image scanner 78, with the optical distance from variable focus lens 58 and the straight line distance of the diverting prism 121 to the dental target determined by image scanner 78, and the focus of the light and laser beams varied in accordance therewith by the error signal generator 79, the electromagnetic impulser 81, cylinder 83, and conduit 22. Since the adjustment of the variable focus lens 58 is substantially instantaneous, the dental operator may be able to effect removal of material on the dental target even though the distance between the diverting prism 121 and the dental target will change due to either or both of the following conditions. One condition is that the dental handpiece 120 may be moved so as to cause the beam to traverse a surface or region of the dental target which is curved, and the operator of the handpiece 120 will not be able to maintain the diverting prism 121 at a precise distance from the dental target as the beam is moved over the curving surface thereof. The other condition, which is also overcome by the present invention, is the inability of a dental operator to maintain the dental handpiece and particularly the diverting prism 121 at a precise distance, even from a plane surface, should such be encountered in or on the teeth T. For either of these causes or conditions, it will be appreciated that the physical distance from the diverting prism 121 to the dental target site will vary, but such variation will be sensed, and there will be caused the automatic focussing of the localized energy focus spot of the laser beam on the surface of the dental target site through the above described exemplary focussing apparatus.

The claims and the specification describe the invention presented, and the terms that are employed in the claims draw their meaning from the use of such terms in the specification. Some terms employed in the prior art may be broader in meaning than specifically employed herein. Whenever there is a question between the broader definition of such term as used in the prior art and the more specific use of the term herein, the more specific meaning is meant.

What is claimed is:

1. Apparatus for performing surgery upon a subject body comprising:
    means for emitting leaser radiation,
    a handpiece,
    means comprising a variable focus lens in said handpiece for receiving laser radiation from said laser radiation emitting means and for sharply focussing said laser radiation to a localized spot at a position beyond said handpiece,
    means for sensing through said variable focus lens an image of an object beyond said handpiece and a focus of the image and for generating a control signal representative of the focus of an a image sensed by said focus sensing means, and
    means for adjusting said variable focus lens in response to said control signal for changing the position of said localized spot towards or from said object.

2. The apparatus of claim 1, said focus sensing means further comprising a low alignment laser beam for illuminating the object.

3. The apparatus of claim 1, said focus sensing means comprising means for radiating said object, means for scanning an image of said object, and means for conducting radiation from said object to said image scanning means.

4. The apparatus in accordance with claim 1, wherein said means for sensing the focus of an image comprises a coupling lens, said handpiece having a proximal end and a distal end, said coupling lens being at said distal end of said handpiece, and wherein said coupling lens is a plano convex lens having a plano side and a convex side, said plano side being an exterior surface of said handpiece located at the distal end thereof.

5. Apparatus for performing surgery upon a subject body as set forth in claim 1, wherein said means for sensing the focus of an image comprises a coupling lens, said handpiece having a proximal end and a distal end, said coupling lens being at said distal end of said handpiece.

6. The apparatus in accordance with claim 5, and wherein said coupling lens is a plano convex lens, having a plano side and a convex side, said plano side being an exterior surface of said handpiece located at the distal end of said handpiece.

7. The apparatus of claim 1, said focus sensing means comprising second means for emitting radiation, means for directing radiation from said second means for emitting radiation to said object, and means for receiving emitted radiation reflected from the object and for generating said control signal.

8. The apparatus of claim 7, said second radiation emitting means comprising a source of visible light.

9. The apparatus of claim 7, said means for receiving emitted radiation comprising a fiberoptic bundle connected to said handpiece to thereby receive an image of the object, said handpiece comprising an elongate, generally cylindrical member having proximal and distal ends, an optical path extending longitudinally through said handpiece, said fiberoptic bundle having an end coupled to said proximal end of said handpiece and having a terminal portion in alignment with the optical path, a television camera coupled to said fiberoptic bundle, means for projecting an image of said object from said fiberoptic bundle to said television camera, and a television monitor connected with said television camera for displaying an image of said object.

10. The apparatus of claim 1, said handpiece having a means for turning a light beam therein, a first optical path in said handpiece passing through said variable focus lens, a second optical path having a part thereof in said handpiece transverse to said first optical path, said optical paths meeting at a juncture and said light beam turning means located at the juncture of said optical paths.

11. The apparatus of claim 10, said apparatus further comprising a source of light, a fiberoptic bundle connected to said handpiece for conducting light from the source of light and the object into and from said handpiece along said first optical path.

12. The apparatus of claim 11, wherein said focus sensing means comprises said fiberoptic bundle, a source of light, means for introducing light from said source of light into said fiberoptic bundle to thereby illuminate said object and generate an image thereof, image scanning means for receiving the image of said object and for generating a signal representative of a focus condition of said light on said object, and signal generating means for receiving said signal, comparing said signal with a predetermined signal value, and for generating said control signal.

13. An apparatus for use at an operational site comprising:
    (a) an elongate handpiece having at least one optical path therein and proximal and distal ends.
    (b) a variable focus lens in said handpiece along said optical path,
    (c) means for directing laser radiation into said handpiece to said variable focus lens,
    (d) means for passing radiation to an operational site beyond said distal end through said variable focus lens, and means for acquiring a radiation image of the operational site through said variable focus lens,
    (e) a coupling lens at the distal end of said handpiece for engaging a body to be subjected to laser radiation and for receiving and transmitting radiation passed through said variable focus lens, and
    (f) means for varying said variable focus lens in response to the image of said operational site acquired by said image acquiring means to provide a focussed radiation image of said operational site to said means for acquiring a radiation image.

14. An apparatus for performing surgery by laser radiation at an operational site within a body comprising:

(a) an elongate handpiece having at proximal and distal ends and having an optical path therein, (b) a variable focus lens in said handpiece positioned on optical path, (c) a coupling lens on said optical path at the distal end of said handpiece having an exterior surface for engaging a body to be subjected to laser radiation and for receiving and transmitting radiation passed through said variable focus lens, (d) means for directing laser radiation into said handpiece for passage along said optical path to said variable focus lens, (e) means connected to said handpiece for acquiring an image of the operational site through said variable focus lens and said coupling lens, and (f) means for varying the focus of said variable focus lens comprising means for sensing the image of the site acquired by said image acquiring means through said variable focus lens and said coupling lens, and for varying the focus of said variable focus lens to acquire a focussed image of the operational site to thereby enable laser radiation passing through said variable focus lens and said coupling lens to be focussed in relation to said operational site.

15. The apparatus of claim 14, said image acquiring means comprising a fiberoptic bundle connected to the proximal end of said handpiece, said fiberoptic bundle having an end on said optical path positioned to receive an image of the site, a television camera coupled to said optical fiber and positioned to receive an image of the site from the fiberoptic bundle, and a television monitor connected to said television camera.

16. The apparatus of claim 14, and an imaging coupling lens adjacent the proximal end of said handpiece and positioned along said optical path, comprising means for receiving and focussing, with said variable focus lens and said coupling lens, an image of said operational site.

17. The apparatus of claim 16, wherein said image acquiring means comprises an optical fiber bundle having an end at the proximal end of said handpiece and positioned to receive an image of said operational site from said imaging lens.

18. The apparatus of claim 14, and further comprising means for supporting said handpiece for movement with six degrees of freedom, and means for counterbalancing said handpiece.

19. The apparatus of claim 18, wherein said image acquiring means comprises a flexible optical fiber bundle connected to said handpiece, and wherein said variable focus lens comprises a movable mounted lens hermetically connected to a flexible bellows to provide an expansible chamber, and a flexible conduit fluid connected to said expansible chamber and to means for expanding and contracting said expansible chamber.

20. The apparatus in claim 14, wherein said coupling lens is a plano-convex lens having a convex side and plano side, the plano side being the exterior surface of said coupling lens.

21. The apparatus of claim 20, and in combination therewith a contact lens having a surface engaged by said plano side of said coupling lens.

22. The apparatus of claim 20, wherein said coupling lens is sapphire.

23. The apparatus of claim 14, said variable focus lens comprising:

(a) first and second lenses, (b) means for mounting the first lens in fixed position in said handpiece, (c) means for guiding said second lens along said optical path, (d) an expansible chamber comprising said first and second lenses and a flexible bellows hermetically attached to said first and second lens containing a volume of fluid, and (d) a fluid conduit connected to and in fluid communication with said flexible bellows.

24. The apparatus of claim 23, and further comprising means connected to said fluid conduit for changing the volume of fluid in said expansible chamber.

25. The apparatus of claim 24, said image sensing means comprising means for scanning an image of said site form said image acquiring means and for producing signal representative of the image scanned, said focus varying means comprising error signal generating means for receiving said signal from said image sensing means and for generating an error signal, and control means for receiving said error signal and for actuating said volume changing means to correspondingly change the volume of fluid in said expansible chamber.

26. A method of performing surgery utilizing laser energy comprising:

(a) passing an illuminating beam through an optical system comprising a variable focus lens to an object, and thereafter passing an image of the object through said optical system, said image having a focus condition, (b) sensing the focus condition of said image of said object and any departure from focus of said image after the passing of said illuminating beam through said variable focus lens from said object, (c) changing the focus of said variable focus lens to obtain an image of said object which is in focus, (d) generating a laser beam, and (e) focussing said laser beam to a focus spot relative to the object by passing said laser beam through said variable focus lens after the changing of the focus of said variable focus lens, to thereby cause the laser beam to have a focus spot on or at a predetermined distance from said object.

27. The method of claim 26, wherein said sensing is by receiving a light image of said object and scanning said light image, and thereafter generating a signal representative of the focus condition of the image scanned.

28. The method of claim 26, and further comprising passing said laser beam to a light turning optical element and then to said variable focus lens.

29. The method of claim 26, and further comprising engaging a transparent anatomical part with an element fixed relative to said variable focus lens, and wherein said sensing is of the focus of said variable focus lens with respect to a reference at the engaged transparent anatomical part.

30. The method of claim 26, wherein said sensing is of the focus condition of said variable focus lens of a dental target located on or in a tooth.

* * * * *